United States Patent [19]

Ashworth et al.

[11] 4,323,516

[45] Apr. 6, 1982

[54] METHOD FOR MAKING THIOBISCARBAMATES

[75] Inventors: Robert W. Ashworth, Hackettstown, N.J.; Wallace Y. Fu, South Charleston, W. Va.

[73] Assignee: Union Carbide Corporation, Danbury, Conn.

[21] Appl. No.: 199,382

[22] Filed: Oct. 21, 1980

Related U.S. Application Data

[63] Continuation-in-part of Ser. No. 70,535, Sep. 5, 1979, Pat. No. 4,256,655.

[51] Int. Cl.$^3$ ............................................. C07C 119/18
[52] U.S. Cl. ................................................. 260/453.3
[58] Field of Search ......................... 260/453.3, 453.99

[56] References Cited

U.S. PATENT DOCUMENTS 4,004,031 1/1977 Drabek .............................. 260/453.3

OTHER PUBLICATIONS

R. C. Paul, et al., Indian Journal of Chemistry, 8, 1020 (1970).
V. Wannagat and G. Schindler, Angew. Chem., 69, 784 (1957).

*Primary Examiner*—Henry R. Jiles
*Assistant Examiner*—Robert C. Whittenbaugh
*Attorney, Agent, or Firm*—William Raymond Moran

[57] ABSTRACT

Method of preparing thiobiscarbamates by reacting nitrogen-containing heterocyclic base and sulfur monochloride or sulfur dichloride and reacting the resulting base-sulfur chloride adduct with carbamate to form thiobiscarbamates.

2 Claims, No Drawings

METHOD FOR MAKING THIOBISCARBAMATES

This appication is a continuation-in-part of Ser. No. 70,535, filed Sept. 5, 1979, now U.S. Pat. No. 4,256,655.

BACKGROUND

This invention relates to the manufacture of thiobiscarbamates having the formula $$\left( \begin{array}{c} CH_3-C=N-O-C-N-\\ \phantom{xx}|\phantom{xxxxxxxx}\|\phantom{x}|\\ S-R_1\phantom{xxx}O\phantom{xx}CH_3 \end{array} \right)_2 S \quad (I)$$

wherein $R_1$ is methyl, ethyl, n-propyl, isopropyl, n-butyl or isobutyl and $$\left( \begin{array}{c} \phantom{xxxxxxxx}O\\ \phantom{xxxxxxxx}\|\\ R_2-C=N-O-C-N-\\ \phantom{xx}|\phantom{xxxxxxxxxx}|\\ R_3\phantom{xxxxxxx}CH_3 \end{array} \right)_2 S \quad (II)$$

wherein $R_2$ is methyl, ethyl, n-propyl, isopropyl, n-butyl, isobutyl, or $CH_3S(CH_3)_2C-$ and $R_3$ is H or $CH_2X$ where X is $-SCH_3$, $$-\overset{O}{\underset{}{\overset{\|}{S}}}-CH_3, \quad \text{or} \quad -\overset{O}{\underset{\underset{O}{\|}}{\overset{\|}{S}}}-CH_3.$$

These Biscarbamate compounds are known to have pesticidal activity.

U.S. Pat. No. 4,004,031 discloses a method of making these compounds involving simultanteous reaction of carbamate, base, and sulfur chloride ($SCl_2$ or $S_2Cl_2$). A disadvantage of this prior art method is its relatively low yield of products and high production of undesirable bi-products.

OBJECTS

It is an object of this invention to provide a method for making thiobiscarbamate compounds that produces higher yields.

It is another object of this invention to provide a method for making thiobiscarbamate compounds that produces less biproduct.

SUMMARY OF THE INVENTION

These and other objects are attained by the present invention one aspect of which comprises:

A method for making a compound of the formula $$\left( \begin{array}{c} CH_3-C=N-O-C-N-\\ \phantom{xx}|\phantom{xxxxxxxx}\|\phantom{x}|\\ S-R_1\phantom{xxx}O\phantom{xx}CH_3 \end{array} \right)_2 S$$

wherein R, is methyl, ethyl, n-propyl, isopropyl, n-butyl or isobutyl comprising the steps of:

(a) in represent of solvent, reacting nitrogen-containing heterocyclie base with a sulfur chloride selected from the groups of $SCl_2$, $S_2Cl_2$, and mixtures thereof to form base-sulfur chloride adduct, and thereafter (b) in presence of solvent, reacting said adduct with carbamate of the formula $$\begin{array}{c} CH_3-C=N-O-C-N-H\\ \phantom{xx}|\phantom{xxxxxxxx}\|\phantom{x}|\\ S-R_1\phantom{xxx}O\phantom{xx}CH_3 \end{array}$$

wherein R, is as previously defined.

A second aspect of the invention comprises:

A method for making a compound of the formula $$\left( \begin{array}{c} \phantom{xxxxxxxx}O\\ \phantom{xxxxxxxx}\|\\ R_2-C=N-O-C-N-\\ \phantom{xx}|\phantom{xxxxxxxxxx}|\\ R_3\phantom{xxxxxxx}CH_3 \end{array} \right)_2 S$$

wherein $R_2$ is methyl, ethyl, n-propyl, iospropyl, n-butyl, or $CH_3S(CH_3)_2C-$ and $R_3$ is H or $-CH_2X$ wherein X is $-SCH_3$, $$-\overset{O}{\underset{}{\overset{\|}{S}}}-CH_3 \quad \text{or} \quad -\overset{O}{\underset{\underset{O}{\|}}{\overset{\|}{S}}}-CH_3$$

comprising the steps of (a) in presence of solvent, reacting nitrogen-containing heterocyclic base with a sulfur chloride selected from the groups of $SCl_2$, $S_2Cl_2$, and mixtures thereof to form base-sulfur chloride adduct, and (b) in presence of solvent, reacting said adduct with carbamate of the formula $$\begin{array}{c} \phantom{xxxxxxxx}O\\ \phantom{xxxxxxxx}\|\\ R_2-C=N-O-C-N-H\\ \phantom{xx}|\phantom{xxxxxxxxxx}|\\ R_3\phantom{xxxxxxx}CH_3 \end{array}$$

wherein $R_2$ and $R_3$ are as previously defined.

This invention is predicated on the discovery that complexing nitrogen-containing heterocyclic base with sulfur chloride in presence of a solvent to form an adduct and thereafter reacting carbamate with the adduct provides a surprising increase in yield. This change in the order of addition of the reactants over that of the prior art is especially effective if the solvent is xylene, and if the sulfur chloride used is $SCl_2$.

DETAILED DESCRIPTION OF THE INVENTION

The first step in making thiobiscarbamate compound in accordance with the present invention is to react nitrogen-containing heterocyclic base and sulfur chloride in presence of solvent to form base-sulfur chloride adduct, believed to occur in accordance with the following equation:

$$2\,B + SCl_2 \longrightarrow \begin{array}{c} B-S-B\\ +\phantom{xx}+\\ Cl^-\phantom{x}Cl^- \end{array}$$

base sulfur dichloride    adduct or

-continued

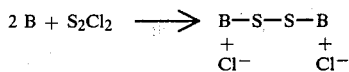

Base sulfur mono chloride     adduct

Preferably sufficient base is used so that all of the sulfur chloride is reacted. The preferred bases are pyridine and 2-ethyl-5-methyl pyridine.

The most preferred solvents are commercial grade xylene and pyridine. However many solvents are acceptable, including but not limited to halogenated hydrocarbons such as dichloromethane, chloroform, carbon tetrachloride, tetrachloroethane; ethers such as diethyl ether, tetrahydrofuran, 1,4-dioxane, diisopropyl ether, diphenyl ether, anisole; aromatic solvents such as benzene, toluene, o-xylene, m-xylene, p-xylene, ethylbenzene, mesitylene, t-butylbenzene, chlorobenzene, nitrobenzene; and other organic solvents such as N,N-dimethylacetamide, N,N-dimethylformamide, acetonitrile, hexane, cyclohexane and methylcyclohexane.

Sulfur dichloride is the preferred sulfur chloride. However, this compound decomposes slowly according to the equation

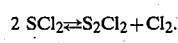

Hence commercial $SCl_2$, which currently is believed to contain roughtly 70 to 85% $SCl_2$, is a practical and acceptable sulfur chloride. Sulfur monochloride, $S_2Cl_2$, is also acceptable, as are mixtures of $SCl_2$ and $S_2Cl_2$.

The reaction between base and sulfur chloride is preferably carried out for about 0.25 to 1 hour at temperatures between and $-10°$ and $50°$ C. More preferably the reaction temperature is about $-10°$ C. to $30°$ C. and the reaction time about 20 min to 60 min.

The second step in the process is to react the adduct with carbamate in the presence of solvent. A preferred carbamate is methomyl. With pyridine as the base, the reaction between methomyl and base-sulfur dichloride adduct is belived to proceed as follows:

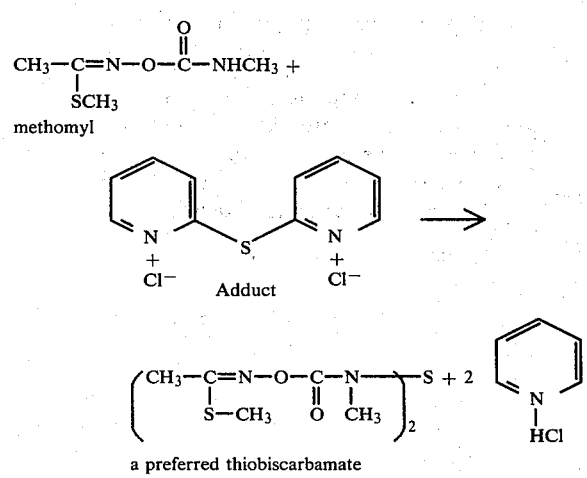

The solvents acceptable for the first step in the process, the adduct forming step, are also acceptable for the second step, the reaction with carbamate. The preferred solvents for the second step are again pyridine and xylene, but other solvents are acceptable. Since the first step yields an adduct-solvent mixture, preferably the second step is performed by adding carbamate to the adduct-solvent mixture resulting from the first step. Of course, the adduct could be separated from the solvent used for the first step and a different solvent used for the second step, but such extra processing is not necessary.

The second step is preferably carried out at a temperature of from about $0°$ C. to $45°$ C., more preferably about $15°$ C. to $32°$ C., and for a reacton time of about 1 hour to 96 hours, more preferably about 1 hour to 20 hours.

When pyridine is used as both solvent and base, purification of the product mixture from the second step is preferably effected by washing and/or slurrying with water or C-1 to C-5 alcohol.

EXAMPLES

Examples 1 to 12 illustrate practice of the invention and examples 13 to 28 illustrate the prior art method. All experiments were conducted under nitrogen atmosphere in a 500 ml, four-necked flask equipped with a thermometer, a mechanical stirrer, a drying tube, and a pressure equalizing addition funnel attached to a nitrogen inlet tube. The assembled apparatus was dried with a heat gun under a nitrogen atmosphere prior to the experiments.

PROCEDURE FOR EXAMPLES 1 to 10

The first step was performed as follows:

The adduct was formed by preparing a solution of 28.5 g. pyridine and 200 g. solvent at about $2°$ C. Sulfur chloride in the amount of 20.74 grams was added to the solution dropwise over a 15 minute period while maintaining temperature of $2°-4°$ C. The adduct precipitated. The adduct-solvent mixture was stirred for 30 minutes.

The second step in the process was performed as follows:

Methomyl in the amount of 53.53 g was added to the mixtures and the temperature was allowed to rise to the reaction temperature. This temperature was maintained for the reaction time while stirring.

The reaction mixture was filtered and the cake washed twice with a 150 g of fresh solvent. The filtered cake was then washed four times with 150 g of water at $40°$ C. The cake was dried and analyzed for purity of the thiobiscarbamate compound. The yield was calculated multiplying the weight of the dried filter cake by the purity in weight % and dividing the theoritical yield of the biscarbamate compound. The results appear in Table I.

PROCEDURE FOR EXAMPLES 11 and 12

These experiments were preformed the same as example 1 to 10 except as noted in foot notes c and d in Table I.

TABLE I

EXAMPLES USING THE PRESENT INVENTION

| EXAMPLE | SOLVENT | SULFUR[a] CHLORIDE | 2ND STEP REACTION TIME (HR) | 2ND STEP REACTION TEMP (°C.) | DRIED CAKE WT. (g) | PURITY | % ABS* YIELD |
|---|---|---|---|---|---|---|---|
| 1 | Toluene | $SCl_2$ | 4 | 30 | 32.76 | 97.5 | 64.9 |
| 2 | Toluene | $SCl_2$ | 5 | 30 | 37.04 | 96.5 | 62.8 |
| 3 | Toluene | $SCl_2$ | 16 | 35 | 37.24 | 98.7 | 62.8 |
| 4 | Xylene[b] | $SCl_2$ | 5 | 25 | 34.08 | 98.4 | 76.6 |
| 5 | Xylene[b] | $SCl_2$ | 11 | 25 | 37.87 | 94.0 | 81.3 |
| 6 | Xylene[b] | $SCl_2$ | 20 | 25 | 55.46 | 96.3 | 91.3 |
| 7 | $CH_2Cl_2$ | $SCl_2$ | 2 | 25 | 30.61 | 93.6 | 49.0 |
| 8 | $CH_2Cl_2$ | $SCl_2$ | 4 | 25 | 31.27 | 94.7 | 50.7 |
| 9 | Ethylbenzene | $SCl_2$ | 20 | 25 | 30.87 | 95.3 | 50.3 |
| 10 | Ethyl ether | $SCl_2$ | 20 | 25 | 46.63 | 89.5 | 71.4 |
| 11[c] | Toluene | $S_2Cl_2$ | 16 | 40 | 44.60 | 98.2 | 74.9 |
| 12[d] | Xylene | $SCl_2$ | 66 | 25 | 48.96 | 90.2 | 75.5 |

[a]Commercial grade $SCl_2$ believed to be about ≦85% $SCl_2$ by wt.
[b]Commercial grade mixed xylene containing about 19% o, 42% m, 18% p xylene and 21% ethylbenzene.
[c]Sulfur monochloride (23.13 g) was added to a solution of 27.10 g of pyridine in 250 ml of toluene at 25–30° C. After 15 minutes, 53.53 g of methomyl was added at once and then heated to 40° C. for 16 hours. After filtration, toluene washing and water washing, the product was vacuum dried to give 44.60 g of product.
[d]2-Ethyl-5-methylpyridine (46.3 g) was substituted for pyridine.

PROCEDURE FOR EXAMPLES 13 TO 28

A suspension of 50 g methomyl, 25 g base, and 300 ml solvent was prepared and warmed to the reaction temperature. To the suspension was added 16.5 g sulfur chloride dissolved in 20 ml solvent. The reaction temperature was maintained for the reaction time listed in the table. The resulting slurry was filtered and the cake washed with 300 ml of cold water twice, and then triturated twice with 300 ml of methanol and filtered. The solid was vacuum dried at 45° C. for 2 hours. The results are listed in Table II. The yield was calculated the same way it was for Examples 1 to 12.

Variations to the above procedure for certain examples are described in the foot note to Table II.

The superiority of the present invention can readily be seen by comparing examples 4, 5 and 6 wherein yields of 76.6, 81.3 and 91.3% were attained, with prior art examples 17, 20 and 22 wherein yields of only 70.7, 60.9 and 56.9 were attained using the same or similar solvent and the same base. Further evidence of the present methods superiority can be ascertained by comparing examples 7 and 8 (49.0 and 50.7% yields) with prior art example 13 wherein only 37.1% yield was attained using $CH_2Cl_2$ as the solvent, and pyridine as the base in both methods.

Example 11 shows that good yields (here 74.9%) can be attained by the present invention using $S_2Cl_2$. Likewise, example 12 shows that the present invention can achieve a good yield with 2-ethyl-5-methyl pyridine as the base.

EXAMPLE 29

Reaction Using Pyridine as Both Solvent and Base

The first step was performed as follows:

The adduct was formed by adding 23 grams of sulfur dichloride to 90 grams of pyridine dropwise over a period of about 15 minutes at 5° C. The adduct precipitated to form an adduct slurry.

TABLE II

EXAMPLE USING PRIOR ART METHOD

| EXAMPLE | SOLVENT | SULFUR CHLORIDE | BASE | REACTION TIME(HR) | REACTION TEMP(°C.) | WT. OF PRODUCT (g) | PURITY (BY LC) | % ABS* YIELD |
|---|---|---|---|---|---|---|---|---|
| 13 | $CH_2Cl_2$ | $SCl_2$ | pyridine | 16 | −10 to 25 | 22.40 | 90.9 | 37.1 |
| 14 | Toluene | $SCl_2$ | pyridine | 48 | 20 to 28 | 40.99 | 97.4 | 70.4 |
| 15[a] | $CH_3CN$ | $SCl_2$ | pyridine | 16 | 25 to 35 | 2.96 | 94.9 | 4.9 |
| 16 | Hexane | $SCl_2$ | pyridine | 16 | 25 to 40 | 27.08 | 91.5 | 43.7 |
| 17 | p-Xylene | $SCl_2$ | pyridine | 16 | 20 to 30 | 41.55 | 96.4 | 70.7 |
| 19[a] | DMF | $SCl_2$ | pyridine | 20 | 0 to 10 | 37.25 | 92.1 | 60.5 |
| 20 | o-Xylene | $SCl_2$ | pyridine | 18.5 | 20 to 30 | 39.09 | 89.1 | 60.9 |
| 21 | Ethylbenzene | $SCl_2$ | pyridine | 4 | 30 | 29.34 | 94.1 | 47.0 |
| 22 | Xylenes | $SCl_2$ | pyridine | 4 | 30 | 38.03 | 87.5 | 56.9 |
| 23 | Toluene | $SCl_2$ | TEA[c] | 19 | 23 | 13.88 | 82.3 | 15.3 |
| 24 | p-Xylene | $SCl_2$ | quinoline[d] | 2 | 25 | 32.64 | 64.3 | 37.0 |
| 25 | Cyclohexane | $SCl_2$ | methylethylpyridine[e] | 1 | 30 | 27.24 | 85.4 | 41.0 |
| 26 | Toluene | $SCl_2$ | isoquinoline[f] | 16 | 35 | 38.07 | 85.36 | 57.29 |
| 27 | $CH_2Cl_2$ | $S_2Cl_2$ | pyridine | 18 | 35 | 33.58 | 89.0 | 64.5 |
| 28[b] | THF/Benzene | $S_2Cl_2$ | pyridine | 10 | 0 | 7.00 | 95.2 | 18.9 |

[a]$SCl_2$ was added without solvent dilution.
[b]Done exactly as described in U.S. Pat. No. 4,004,031 (Ciba-Geigy) issued January 18, 1977.
[c]Triethylamine (36 g) was substituted for the pyridine.
[d]Quinoline (40.81 g) was substituted for the pyridine.
[e]Methylethylpyridine (40.81 g) was substituted for the pyridine.
[f]Isoquinoline (40.81 g) was substituted for the pyridine.

The second step was performed as follows:

Into a separate reactor was placed 53.5 grams of methomyl and 60 grams of pyridine. The resulting mixture was stirred until the methomyl dissolved. The solution was maintained at a temperature of 20° C. to 25° C.

The adduct slurry was pumped into the methomyl (pyridine solution was stirring while maintaining a reaction temperature of 20° C. to 25° C. Adduct addition was comleted after about 1 hour. A reaction temperature of 20° C. to 25° C. was maintained for an additional four hours for the resulting mixture.

Purification of product was effected as follows: 300 grams of methanol was added to the above mixture to form a slurry. The slurry was then cooled to −5° C. with stirring. The slurry was filtered to form a filter cake. The filter cake was washed with 150 grams of methanol at −5° C. The filter cake was then re-slurried in 150 grams of methanol at −5° C. The re-slurry was filtered and then washed twice with 150 grams of methanol at −5° C. The cake was dried in a vacuum over at 40° C. and 40 mm Hg. pressure. The cake consisted of 50.0 grams of product having a melting point of 169° C. to 170° C.

What is claimed is:

1. A method for making a compound of the formula

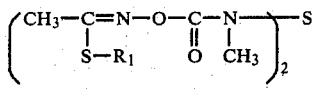

wherein $R_1$ is methyl, ethyl, n-propyl, isopropyl, n-butyl or isobutyl comprising the steps of:
(a) Reacting pyridine with a sulfur chloride selected from the groups of $SCL_2$, $S_2Cl_2$, and mixtures thereof to form pyridine-sulfur chloride adduct, in the presence of excess pyridine, and
(b) reacting said adduct with carbamate of the formula

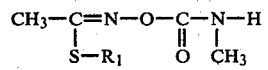

wherein R is as previously defined, in the presence of pyridine.

2. The process of claim 1 which further comprises the step of:
(c) purifying the product of step (b) by washing or slurrying said product at least once with water or C-1 to C-5 alcohol.

* * * * *

United States Patent and Trademark Office
CERTIFICATE OF CORRECTION

PATENT NO. : 4,323,516
DATED : April 6, 1982
INVENTOR(S) : Robert W. Ashworth et al.

It is certified that error appears in the above—identified patent and that said Letters Patent is hereby corrected as shown below:

Column 1, line 61;
   "R," should be --$R_1$--.

Column 1, line 64:
   "heterocyclie" should be --heterocyclic--.

Column 4, line 61;
   "theoritical" should be --theoretical--.

Column 8, line 10;
   "SCL$_2$" should be --$SCl_2$--.

Column 8, line 20;
   "R" should be --$R_1$--.

Signed and Sealed this

Twenty-seventh Day of July 1982

[SEAL]

Attest:

Attesting Officer

GERALD J. MOSSINGHOFF

Commissioner of Patents and Trademarks